US006925333B2

(12) United States Patent
Krebs

(10) Patent No.: US 6,925,333 B2
(45) Date of Patent: Aug. 2, 2005

(54) COMBINATION NEEDLE FOR PERIPHERAL NERVE BLOCK

(76) Inventor: Peter Krebs, Waldstrasse 39, D-78048 Villingen-Schwenningen (DE)

( * ) Notice: Subject to any disclaimer, the term of this patent is extended or adjusted under 35 U.S.C. 154(b) by 472 days.

(21) Appl. No.: 10/151,528

(22) Filed: May 20, 2002

(65) Prior Publication Data

US 2002/0177887 A1 Nov. 28, 2002

(30) Foreign Application Priority Data

May 22, 2001 (DE) ..................... 201 08 558 U

(51) Int. Cl.⁷ ................................. A61N 1/05
(52) U.S. Cl. ......................... 607/116; 606/41
(58) Field of Search .................. 607/116, 117; 600/548, 554; 606/32, 41, 48, 50, 129

(56) References Cited

U.S. PATENT DOCUMENTS

| 3,682,162 A | | 8/1972 | Colyer | |
|---|---|---|---|---|
| 4,248,231 A | * | 2/1981 | Herczog et al. | 606/50 |
| 4,685,904 A | | 8/1987 | Krebs | |
| 4,776,847 A | | 10/1988 | Krebs | |
| 4,892,105 A | * | 1/1990 | Prass | 607/116 |
| 5,007,902 A | * | 4/1991 | Witt | 604/117 |
| 5,853,373 A | * | 12/1998 | Griffith et al. | 600/554 |
| 5,885,219 A | | 3/1999 | Nightengale | |
| 5,976,110 A | * | 11/1999 | Greengrass et al. | 604/158 |
| 6,292,701 B1 | * | 9/2001 | Prass et al. | 607/116 |
| 6,298,256 B1 | * | 10/2001 | Meyer | 600/373 |

FOREIGN PATENT DOCUMENTS

| DE | 35 08 013 | 2/1986 |
|---|---|---|
| DE | 35 08 013 A1 | 2/1986 |
| DE | 36 02 219 A1 | 7/1987 |
| DE | 196 40 670 A1 | 5/1998 |
| EP | 0 823 239 A2 | 2/1998 |

* cited by examiner

Primary Examiner—Kennedy Schaetzle
(74) Attorney, Agent, or Firm—McGlew and Tuttle, P.C.

(57) ABSTRACT

The combination needle is intended for peripheral nerve block. It comprises a plastic cannula (1) and an essentially cylindrical, solid steel mandrel (10), which is provided with a pricking tip, which is free from a cutting edge, and with a grip part (11), which has an electric plug contact (21) for the connection of an electrostimulator. The steel mandrel (10) can be introduced into the cannula (1) such that its pricking tip (42) protrudes from the front end of the cannula or is at least flush with same. It shall be achieved with the present invention that the two ["bei der die beiden" in German original should read "die beiden"—Tr.Ed.] electrodes necessary for the electrostimulation are located at a very short distance from one another and the electric effects of the stimulation is [sic—Tr.Ed.] limited to the body area where the stimulation shall take place. The steel mandrel (10) therefore has a two-pole design and is provided with a two-pole electric plug contact means (21, 37).

14 Claims, 3 Drawing Sheets

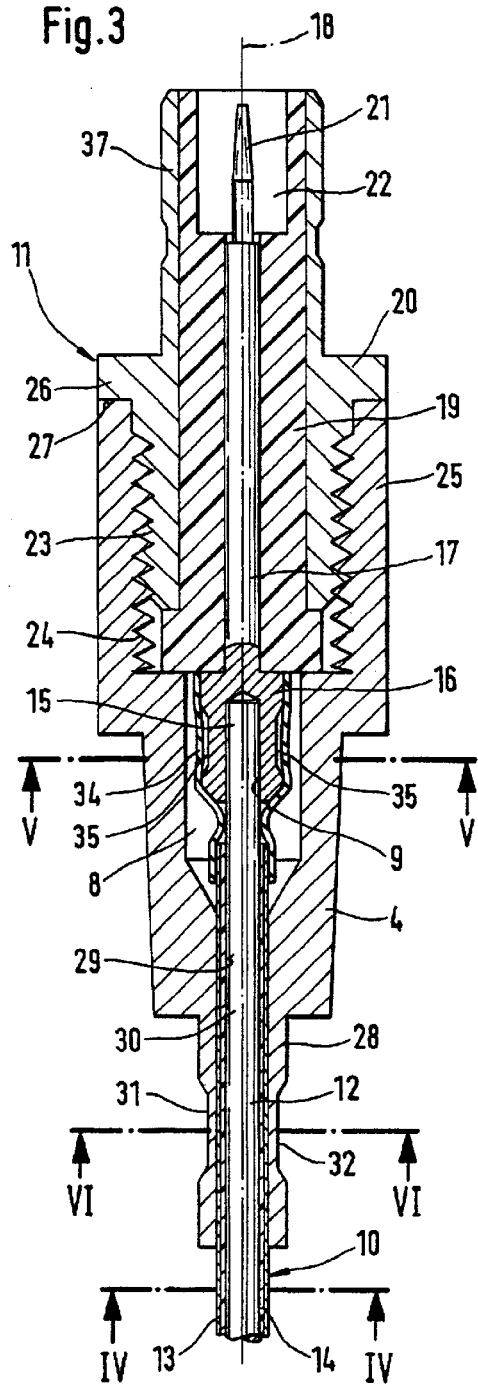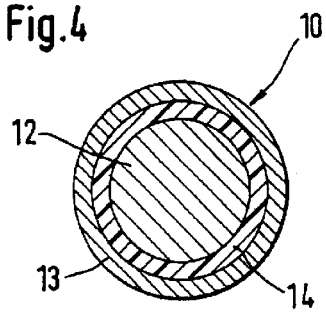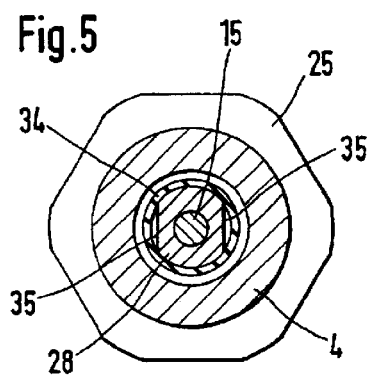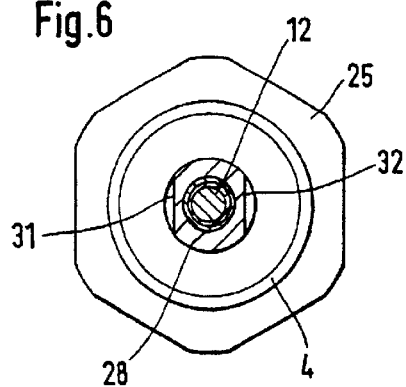

COMBINATION NEEDLE FOR PERIPHERAL NERVE BLOCK

FIELD OF THE INVENTION

The present invention pertains to a combination needle for peripheral nerve block, comprising a plastic cannula and an essentially cylindrical, solid steel mandrel, which is provided with a pricking tip without a cutting edge and with a grip part, which has an electric plug contact for the connection of an electrostimulator, wherein the steel mandrel can be introduced into the cannula such that its pricking tip protrudes from the front end of the cannula or is at least flush with same.

BACKGROUND OF THE INVENTION

A combination needle of this type is known from, e.g., DE 35 08 013 C2. It is used for anesthesia and analgesia of the arm, block of the branchial plexus in the axillary region being preferably performed.

The prior-art combination needle is characterized by special designs of the pricking tip of the steel mandrel comprising a solid bar, which designs are suitable for piercing the nerve sheath consisting of solid tissue, also called neurilemma or fascia, by applying the smallest possible amount of force, and in which the risk of damage to the nerves is reduced to a minimum.

In addition, the particular position of the tip of the needle shall be able to be exactly localized. While the first requirements can be met by the shape of the pricking tip of the steel mandrel alone, the localization of the pricking tip at the nerve tract is performed by electrostimulation, which is carried out by applying an electric voltage of a certain intensity and of short duration. A plug socket is provided for this purpose at the end of the steel mandrel provided with the handle in the prior-art combination needle. Even though an anesthetist can read based on the length scale provided on the jacket surface of the plastic cannula how deep the cannula has penetrated into the skin, the anesthetist cannot determine from this how far the tip of the cannula is located in the vasomotor nerve sheath, because the distance between the vasomotor sheath and the skin surface or the pricking site differs from one patient to the next.

However, this plug socket has only a single-pole design, i.e., only one pole can be connected to a power source at the steel mandrel. The second necessary pole is connected to an electrode, which is placed somewhere outside on the body of the patient in question during the use of this prior-art combination needle. As such, there is a relatively great distance in all cases between the tip of the steel mandrel, which forms one electrode, and the second electrode, which is fastened at a favorable point outside on the patient's body.

From this arises the drawback that larger parts of the body are always affected by the electric effect of the electrostimulation. In patients who are provided with implanted electric devices, e.g., a cardiac pacemaker, this may lead to harmful results, which should be avoided by all means.

SUMMARY OF THE INVENTION

The basic object of the present invention is to provide a combination needle of the type mentioned in the introduction, in which the two electrodes necessary for electrostimulation are located very close to one another and the electric effects of the stimulation are limited to the area of the body where the stimulation is to take place.

This object is accomplished according to the present invention by the mandrel having a two-pole design and being provided with a two-pole electric plug contact devoce.

Using the combination needle designed according to the present invention, it is possible to concentrate the effect of an electrostimulation to the area of the pricking tip of the steel mandrel and to spare all other body parts herefrom. The possibly harmful effects of the electrostimulation, which may occur when the second electrode is placed on an outer point of the patient's body, are ruled out with certainty.

An embodiment of the present invention with one pole formed by the electrically conductive steel core and the second pole formed of a conductive jacket layer, which may be applied to an insulator layer enclosing the jacket surface of the steel core in a closed manner also offers the possibility of manufacturing and handling such a combination needle in a simple manner.

It is also possible with the embodiment wherein the insulator layer is formed of an insulating varnish and the conductive jacket layer is formed of a metal coating applied by electroplating to manufacture very thin steel mandrels or thin combination needles, because the insulator layer and the conductive jacket layer may be very thin. The thickness of such a layer may be, e.g., in the range of 0.005 mm to 0.2 mm.

Further advantageous embodiments of the present invention are disclosed herein, and these embodiments have especially the advantage of offering the possibility of using at least partly commercially available plug-type connections and of manufacturing the contacting connections between the conductive parts of the steel mandrel and the plug part in a purely mechanical manner, i.e., without soldering or welding, in a reliable manner and also with the necessary strength.

An exemplary embodiment of the present invention will be explained in greater detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 3 is a greatly enlarged sectional view of the grip part of the steel mandrel according to the invention;

FIG. 4 is an even more greatly enlarged sectional view along line IV—IV from FIG. 3;

FIG. 5 is a sectional view along line V—V from FIG. 3 on the same scale;

FIG. 6 is a sectional view along line VI—VI from FIG. 3, likewise on the same scale.

DESCRIPTION OF THE PREFERRED EMBODIMENT

Figure 1:
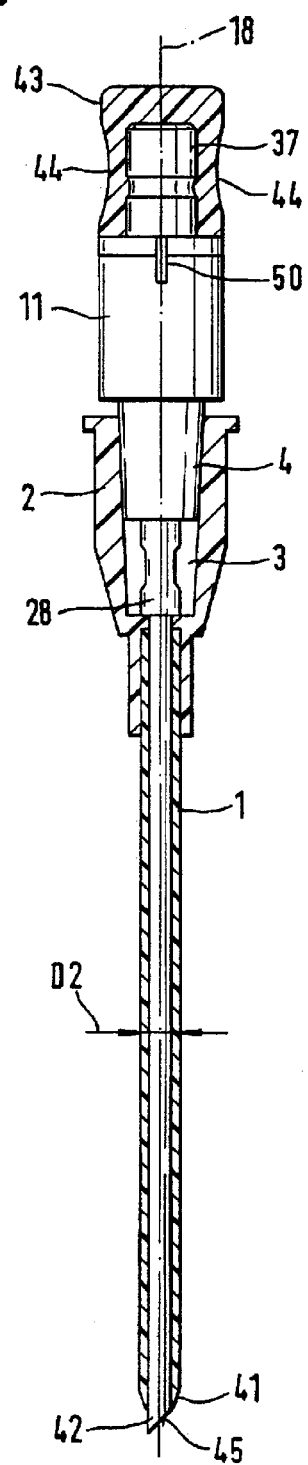
FIG. 1 is a sectional view of the combination needle with the plastic cannula attached according to the invention.
Figure 2:
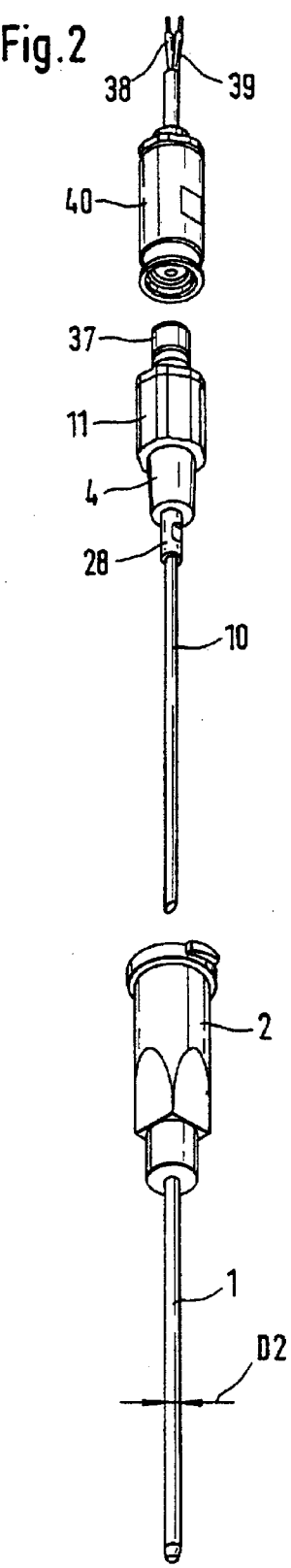
FIG. 2 is an isometric exploded view of the combination needle according to the invention with the steel mandrel with handle and plastic cannula with handle as well as with an electric plug socket.

Referring to the drawings in particular, the combination needle for peripheral nerve block shown in the drawings comprises a plastic cannula 1 and a cylindrical, solid steel mandrel 10. The plastic cannula 1 has a diameter D2 of about 0.8 mm to 1.3 mm, while the diameter D1 of the steel mandrel 10, coordinated with the internal diameter of the plastic cannula 1, may be about 0.6 mm to 1 mm.

The plastic cannula 1 is provided with a handle 2, which likewise consists of plastic and has a rear-side open cavity 3. This cavity 3 has a conical shape, so that it can fittingly accommodate a so-called Luer's cone 4, which is part of a grip part 11 of the steel mandrel 10. The plastic cannula 1 and its handle 2 are firmly connected to one another in the usual manner.

The steel mandrel 10 comprises a solid steel core 12, which forms one pole or one electrode in an electrically conductive manner during the electrostimulation. The steel mandrel 10 has a two-pole design due to the second pole or the second electrode being formed by a conductive metallic jacket layer 13, which is applied to an insulator layer 14 enclosing the jacket surface of the steel core 12 in a closed manner. The insulator layer 14 consists of an insulating varnish, and the conductive jacket layer 13 consists of a metal coating applied by electroplating, preferably nickel, chromium or gold.

The rear end 15 of the steel core, which is freed of the conductive jacket layer 13 and the insulator layer 14, is fastened in a central axial hole 9 of an essentially cylindrical metal part 16 in a contacting manner. This metal part 16 is a one-piece component of a plug pin 17. The plug pin 17 is arranged tightly in an insulator socket 19 of a metallic plug socket 20 coaxially to a central axis 18, and it has a contact tip 21. The contact tip 21 protrudes freely into a cylindrical cavity 22 of the insulator socket 19. The cavity 22 is open on the front side.

The insulator socket 19 is likewise coaxial to the central axis 18. The insulator socket 19 is arranged tightly in the plug socket 20. The plug socket 20 is provided with a threaded shaft 23, which is screwed into a fitting internal thread 24 of a metallic coupling sleeve 25 to the extent that a flange ring 26, preferably designed as a hexagon, is seated on the front-side ring surface 27 of the coupling sleeve 25.

The coupling sleeve 25 and the plug socket 20 can thus be fitted together easily to form the grip part 11. The coupling sleeve 25 is provided on the front side with the above-mentioned Luer's cone 4, which is joined in one piece by a sleeve section 28 of reduced diameter. On the front side, the coupling sleeve 25 is provided with a central axial hole 29, which is coordinated with the diameter D1 of the steel mandrel 10 and in which the rear part 30 of the steel mandrel 10 with the conductive jacket layer 13 and the insulator layer 14 are accommodated. To fasten the steel mandrel 10 in this axial hole 29 in a contacting manner, the sleeve section 28 of reduced diameter is pressed radially together with the steel mandrel 10, forming beads 31 and 32, so that not only is a contacting connection established between the conductive jacket layer 13 of the steel mandrel 10 and the coupling sleeve 23, but a tensile connection is also established between these parts. The threaded connection 23/24 is absolutely necessary here.

The rear end 15 of the steel core 12 is also connected to the plug pin 17 in a contacting and firm manner in the same manner, i.e., by radial pressing of the metal part 16.

The beads 35 and 35 formed by the axial pressing on the metal part 16 are also visible in FIG. 5.

A piece of elastic tube made of insulating material encloses the rear end of the conductive jacket layer 13 and of the insulator layer 14. This piece of elastic tube made of insulating material is pulled over the metal part 16.

To freely mount the metal part 16 covered with the piece of elastic tube 34, the coupling sleeve 25 is provided with a cylindrical hole 8 ending conically at the front end.

At the rear end, the plug socket 20 has a tubular attachment 37, which encloses the rear section of the insulator socket and is used for lockingly mounting a coaxial, commercially available plug socket 40 provided with two plug contacts and two connection lines 38, 39.

The length of the plastic cannula 1 is selected to be such that, as is shown in FIG. 1, it extends with its front, conically tapered end 41 just barely to the pricking tip 42 of the steel mandrel 10 when its handle 2 is pushed tightly over the Luer's cone 4.

The known principles already described in DE 35 08 013 C2 are to be observed concerning the design of the pricking tip. Such pricking tips, which meet the requirements imposed, are shown as examples in FIGS. 7a through 7f.

Figure 7A:
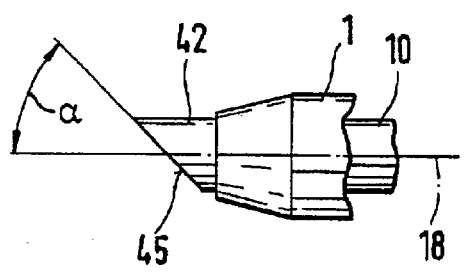
FIG. 7 is a side view of pricking tips of various shapes of the steel mandrel according to the invention.

The pricking tip 42 according to FIG. 7a is ground on one side such that a ground surface 45 is formed, which forms a wedge angle α of 45° with the central axis 18. This ground surface 45 has the geometric shape of an ellipse, which is formed exclusively by the cylindrical jacket surface of the steel mandrel 10 and by the conductive jacket layer 13 and has no facets whatsoever. Sharp cut edges are to be avoided on this pricking tip 42.

Figure 7B:
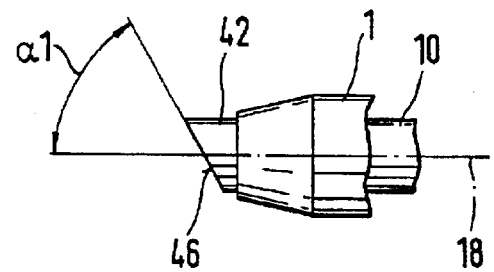

In FIG. 7b, the wedge angle α1 of the ground surface 46 located on one side is 60°. This pricking tip 42 is thus more blunt than the pricking tip 42 according to FIG. 7a. It likewise has no facets and sharp cutting edges.

In the case of these pricking tips 42 of the steel mandrel 10, which are ground on one side, it is important for the user to know after stabbing in the combination needle the particular position of the ground surface 45, 46. A marking 50 (FIG. 1), which may consist of, e.g., a notch and at which the user can recognize the rotation position of the ground surface 45, 46, is therefore provided on the grip part.

Figure 7C:
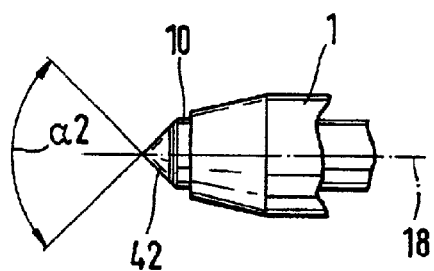

The pricking tip 42 shown in FIG. 7c comprises a straight pointed cone, whose cone angle α2 is 90°.

Figure 7D:
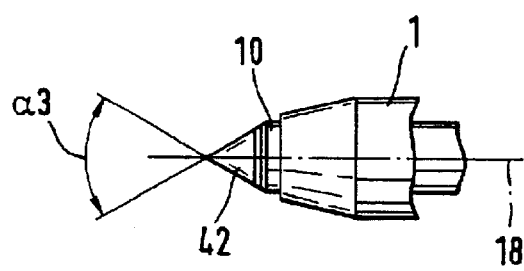

In the likewise conical pricking tip 42 according to FIG. 7d, the cone angle α3 is only 60°; however, the tip of the cone is rounded in the form of a conical section, and the radius of curvature approximately corresponds to half the diameter of the steel mandrel 10.

Figure 7E:
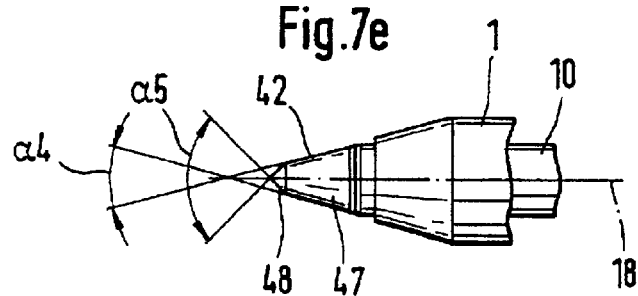

FIG. 7e shows a pricking tip 42 which has a two-stepped conical design and has a more slender section 47 with a cone angle α4 of 30° and a blunter end part 48 with a cone angle α5 of 120°.

Finally, FIG. 7f shows a pricking tip 42 which is designed as a flared cone, whose radius of curvature R approximately corresponds to 1.5 times the diameter D1 of the steel mandrel 10.

It is self-explanatory that the two-pole design of the steel mandrel 10 and of the plug contact means on the grip part 11 does not have a limiting effect on the shaping of the pricking tip 42.

The two-pole character of the combination needle being described is thus given due to the fact that the core part 12 of the steel mandrel 10 is connected in an electrically conductive manner only to the plug pin 17 and the conductive jacket layer 13 of the steel mandrel 10 is connected via the coupling sleeve 25 in an electrically conductive manner only to the plug socket 20 and its tubular attachment 37. The conductive jacket layer 13 is insulated against the core part 12 of the steel mandrel 10 by the insulator layer 14; the coupling sleeve 25 and the plug socket 20, both of which consist of conductive material and are in contact with one another, are insulated against the plug pin 17 by the insulator socket 19.

The handling of the combination needle according to the present invention is not compromised or altered by the two-pole character in any way, aside from the above-mentioned advantages of this two-pole character during the application of the electrostimulation, whose focusing local limitation to the area of the tip of the needle represents a considerable advancement over the prior-art combination needle.

A protective cap 43 made of plastic is provided to improve the handling of the combination needle and to protect at the same time the electric contact elements of the grip part 11, namely, the tubular attachment 37 and the contact tip 21, against harmful external effects. This protective cap 43, which can be easily removed, is placed on the tubular attachment 37, so that it completely surrounds same. It is provided with recessed grips 44 on its circumference to ensure that it can be held firmly with the fingers when putting on and pulling off.

What is claimed is:

1. A combination needle for peripheral nerve block, the needle comprising:
   a plastic cannula;
   an essentially cylindrical solid steel mandrel with a steel core and with a pricking tip which is free of a cutting edge, said steel mandrel being introducable into said cannula such that said pricking tip protrudes from the front end of the cannula or is at least flush with the front end of the cannula;
   a grip part with an electric plug contact for the connection of an electrostimulator, said steel mandrel having a two-pole design and having a two-pole electric plug contact;
   an insulator layer enclosing a surface of said steel core of said cylindrical solid steel mandrel in a closed manner; and
   a conductive jacket layer applied to said insulator layer, wherein one pole is formed by said steel core which is electrically conductive, and another pole comprises said conductive jacket layer.

2. A combination needle in accordance with claim 1, wherein said insulator layer comprises an insulating varnish and said conductive jacket layer comprises a metal coating applied by electroplating.

3. A combination needle in accordance with claim 1, further comprising:
   a metallic plug socket;
   an insulator socket mounted in said metallic plug socket;
   a plug pin having central axial hole said plug pin being mounted in said insulator socket of said metallic plug socket in a contacting manner; and
   a coupling sleeve with a central axial hole provided and with a Luer's cone, wherein a rear end of said steel core, free of said conductive jacket layer and free of said insulator layer is fastened in said central axial hole of a plug pin mounted in an insulator socket of a metallic plug socket in a contacting manner and that a rear section of the conductive jacket layer of the steel mandrel is fastened in said central axial hole said coupling sleeve, provided with said Luer's cone, in a contacting manner.

4. A combination needle in accordance with claim 3, wherein said plug socket and said coupling sleeve are screwed together in a coaxial arrangement.

5. A combination needle in accordance with claim 3, further comprising: an extension connected in one piece to said plug pin and located axially outside said insulator socket, wherein said axial hole accommodating said rear end of said steel core is located in said extension and said extension is radially pressed together with said steel core.

6. A combination needle in accordance with claim 3, wherein said plug-type Luer's cone has a sleeve section of reduced diameter, said sleeve section contacting only said conductive jacket layer and being radially pressed together with said steel mandrel.

7. A combination needle in accordance with claim 3, wherein said plug socket has a tubular attachment enclosing said contact tip of said plug pin and said insulator socket lockingly receives a coaxial plug socket provided with two plug contacts and two connection lines.

8. A peripheral nerve block needle comprising:
   a cannula formed of insulating material;
   an essentially cylindrical steel mandrel with a pricking tip, said mandrel being introduced into said cannula such that said pricking tip protrudes from the front end of the cannula or is at least flush with the front end of the cannula;
   a grip pan with a contact for the connection of an electrostimulator, said steel mandrel having two conductive parts to form two-poles with two-pole electric plug contacts, wherein said two conductive parts comprise a mandrel steel core and a conductive jacket layer and further comprising an insulator layer enclosing a surface of said mandrel steel core and separating said mandrel steel core and said conductive jacket layer.

9. A needle in accordance with claim 8, wherein said insulator layer comprises an insulating varnish and said conductive jacket layer comprises a metal coating applied by electroplating.

10. A needle in accordance with claim 8, further comprising:
    a metallic plug socket;
    an insulator socket mounted in said metallic plug socket;
    a plug pin having central axial hole said plug pin being mounted in said insulator socket of said metallic plug socket in a contacting manner; and
    a coupling sleeve with a central axial hole provided and with a Luer's cone, wherein a rear end of said steel core, free of said conductive jacket layer and free of said insulator layer is fastened in said central axial hole of a plug pin mounted in an insulator socket of a metallic plug socket in a contacting manner and that a rear section of the conductive jacket layer of the mandrel is fastened in said central axial hole said coupling sleeve, provided with said Luer's cone, in a contacting manner.

11. A needle in accordance with claim 10, wherein said plug socket and said coupling sleeve are screwed together in a coaxial arrangement.

12. A needle in accordance with claim 10, further comprising: an extension connected in one piece to said plug pin and located axially outside said insulator socket, wherein said axial hole accommodating said rear end of said steel core is located in said extension and said extension is radially pressed together with said steel core.

13. A needle in accordance with claim 10, wherein said plug-type Luer's cone has a sleeve section of reduced diameter, said sleeve section contacting only said conductive jacket layer and being radially pressed together with said mandrel.

14. A needle in accordance with claim 10, wherein said plug socket has a tubular attachment enclosing said contact tip of said plug pin and said insulator socket lockingly receives a coaxial plug socket provided with two plug contacts and two connection lines.

* * * * *